(12) United States Patent
Levy et al.

(10) Patent No.: US 9,599,572 B2
(45) Date of Patent: Mar. 21, 2017

(54) OPTICAL INSPECTION SYSTEM AND METHOD

(71) Applicant: ORBOTECH LTD., Yavne (IL)

(72) Inventors: Ronen Levy, Tel Aviv (IL); Ofer Saphier, Rehovot (IL); Ariel Danan, Tel Aviv (IL)

(73) Assignee: Orbotech Ltd., Yavne (IL)

( * ) Notice: Subject to any disclaimer, the term of this patent is extended or adjusted under 35 U.S.C. 154(b) by 56 days.

(21) Appl. No.: 14/246,790

(22) Filed: Apr. 7, 2014

(65) Prior Publication Data

US 2015/0285734 A1    Oct. 8, 2015

(51) Int. Cl.
*G01N 21/88* (2006.01)

(52) U.S. Cl.
CPC . *G01N 21/8806* (2013.01); *G01N 2201/0697* (2013.01); *G01N 2201/06113* (2013.01)

(58) Field of Classification Search
CPC .......................... G01N 21/21; G01N 21/8806
See application file for complete search history.

(56) References Cited

U.S. PATENT DOCUMENTS

| | | | |
|---|---|---|---|
| 4,992,949 A * | 2/1991 | Arden | ............ 700/223 |
| 5,309,277 A | 5/1994 | Deck | |
| 5,349,440 A | 9/1994 | DeGroot | |
| 5,580,471 A | 12/1996 | Fukumoto et al. | |
| 5,745,176 A | 4/1998 | Lebens | |
| 6,028,306 A | 2/2000 | Hayashi | |
| 6,102,552 A | 8/2000 | Tullis | |
| 6,191,802 B1 * | 2/2001 | Kessler | ............ B41M 3/06 347/225 |
| 6,236,454 B1 | 5/2001 | Almogy | |
| 6,249,381 B1 | 6/2001 | Suganuma | |
| 6,880,952 B2 | 4/2005 | Kiraly et al. | |
| 7,090,357 B2 | 8/2006 | Magarill et al. | |
| 7,229,202 B2 | 6/2007 | Sander | |
| 7,260,298 B2 | 8/2007 | Furman et al. | |
| 7,319,229 B2 | 1/2008 | Vaez-Iravani et al. | |

(Continued)

FOREIGN PATENT DOCUMENTS

WO    2008/029337 A1    3/2008

OTHER PUBLICATIONS

Communication dated Aug. 16, 2015 issued by the International Searching Authority in counterpart International Application No. PCT/IL2015/000016.

*Primary Examiner* — Tarifur Chowdhury
*Assistant Examiner* — Omar Nixon
(74) *Attorney, Agent, or Firm* — Sughrue Mion, PLLC

(57) ABSTRACT

An optical inspection system including a first multiplicity of cameras operative to image a second multiplicity of regions on an object, a third multiplicity of illumination sources and at least one illumination manager operative to combine illumination from the third multiplicity of illumination sources and thereafter to direct illumination therefrom to the second multiplicity of regions, the at least one illumination manager including a beam distributor receiving a composite input beam of a multiplicity of non-mutually coherent, spatially concentrated laser pulses and directing a multiplicity of composite output beams of a plurality of the non-mutually coherent, spatially concentrated laser pulses to a corresponding plurality of spatially distinct locations corresponding to the second multiplicity of regions.

19 Claims, 6 Drawing Sheets

(56) References Cited

U.S. PATENT DOCUMENTS

| | | |
|---|---|---|
| 7,520,642 B2 | 4/2009 | Holman et al. |
| 7,565,049 B2 | 7/2009 | Sugita et al. |
| 7,659,973 B2 | 2/2010 | Furman et al. |
| 7,714,996 B2 | 5/2010 | Yan et al. |
| 7,843,559 B2 | 11/2010 | Furman et al. |
| 7,850,334 B2 | 12/2010 | Holder et al. |
| 7,961,763 B2 | 6/2011 | Furman et al. |
| 7,988,305 B2 | 8/2011 | Itoh et al. |
| 8,355,190 B2 | 1/2013 | Leister |
| 8,390,926 B2 | 3/2013 | Bordenyuk |
| 2001/0023921 A1* | 9/2001 | Mano .......................... 250/234 |
| 2002/0093832 A1 | 7/2002 | Hamilton |
| 2003/0202361 A1 | 10/2003 | Johnston, II et al. |
| 2004/0145644 A1* | 7/2004 | Makino ....................... 347/233 |
| 2005/0047172 A1 | 3/2005 | Sander |
| 2005/0201097 A1 | 9/2005 | Kiraly et al. |
| 2006/0012778 A1 | 1/2006 | Vaughnn |
| 2006/0245623 A1 | 11/2006 | Loiacono et al. |
| 2007/0291810 A1 | 12/2007 | Luo et al. |
| 2009/0092288 A1* | 4/2009 | Uemura .............. G03F 7/70791 382/106 |
| 2009/0296176 A1 | 12/2009 | Leister |
| 2010/0034227 A1 | 2/2010 | Amundson et al. |
| 2011/0013414 A1 | 1/2011 | Smithson |
| 2011/0044046 A1 | 2/2011 | Abu-Ageel |
| 2011/0102575 A1* | 5/2011 | Case ................. G01N 21/8806 348/87 |
| 2011/0285988 A1 | 11/2011 | Menachem et al. |
| 2012/0087143 A1 | 4/2012 | Hill |
| 2012/0188786 A1 | 7/2012 | Burges |
| 2012/0307512 A1 | 12/2012 | Cogger et al. |
| 2013/0003343 A1 | 1/2013 | Sudarshanam et al. |
| 2013/0293681 A1* | 11/2013 | Borowski ....................... 348/46 |

* cited by examiner

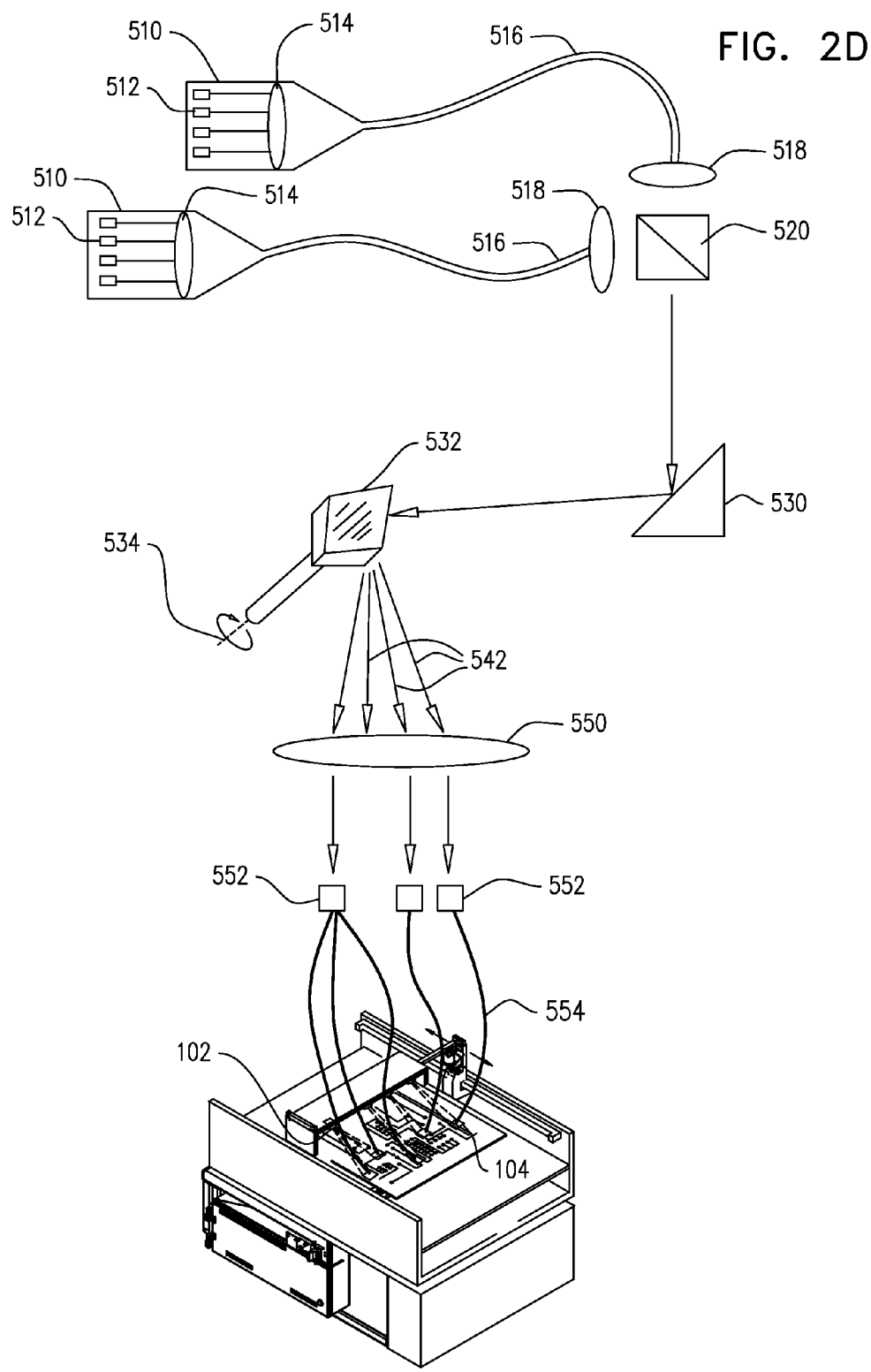

OPTICAL INSPECTION SYSTEM AND METHOD

FIELD OF THE INVENTION

The present invention relates to optical inspection systems generally and more particularly to illumination subsystems useful in optical inspection systems.

BACKGROUND OF THE INVENTION

Various types of optical inspection systems are known as are illumination subsystems useful therein.

SUMMARY OF THE INVENTION

The present invention seeks to provide improved illumination subsystems for use in optical inspection systems.

There is thus provided in accordance with a preferred embodiment of the present invention an optical inspection system including a first multiplicity of cameras operative to image a second multiplicity of regions on an object, a third multiplicity of illumination sources and at least one illumination manager operative to combine illumination from the third multiplicity of illumination sources and thereafter to direct illumination therefrom to the second multiplicity of regions, the at least one illumination manager including a beam distributor receiving a composite input beam of a multiplicity of non-mutually coherent, spatially concentrated laser pulses and directing a multiplicity of composite output beams of a plurality of the non-mutually coherent, spatially concentrated laser pulses to a corresponding plurality of spatially distinct locations corresponding to the second multiplicity of regions.

Preferably, the beam distributor is a time and space beam distributor. Alternatively, the beam distributor is a time beam distributor. Alternatively, the beam distributor is a space beam distributor.

In accordance with a preferred embodiment of the present invention the beam distributor includes a polygon mirror. Alternatively, the beam distributor includes a monogon minor.

Preferably, at least one of the first multiplicity of cameras operates in a strobed mode governed by the timing of arrival of a corresponding at least one of the composite output beams at at least one of the spatially distinct locations. Additionally, operation of the first multiplicity of cameras in the strobed mode is at least partly governed by the at least one illumination manager.

There is also provided in accordance with another preferred embodiment of the present invention an optical inspection system including a first multiplicity of cameras operative to image a second multiplicity of regions on an object, a third multiplicity of illumination sources and at least one illumination manager operative to combine illumination from the third multiplicity of illumination sources and thereafter to separately direct the illumination to the second multiplicity of regions, the at least one illumination manager including a moving mirror receiving a composite input beam of a multiplicity of non-mutually coherent, spatially concentrated laser pulses and directing a multiplicity of composite output beams of a plurality of the non-mutually coherent, spatially concentrated laser pulses to a corresponding plurality of spatially distinct locations.

Preferably, the at least one illumination manager includes a polygon minor. Alternatively, the at least one illumination manager includes a monogon mirror.

In accordance with a preferred embodiment of the present invention at least one of the first multiplicity of cameras operates in a strobed mode governed by the timing of arrival of a corresponding at least one of the composite output beams at at least one of the spatially distinct locations. Additionally, operation of the first multiplicity of cameras in the strobed mode is at least partly governed by the at least one illumination manager.

There is further provided in accordance with yet another preferred embodiment of the present invention an optical inspection method including imaging, using a first multiplicity of cameras, a second multiplicity of regions on an object, combining, using at least one illumination manager, illumination from a third multiplicity of illumination sources and directing, using the at least one illumination manager, the illumination from the third multiplicity of illumination sources to the second multiplicity of regions, the combining including receiving, at a beam combiner, the illumination from the third multiplicity of illumination sources and providing, using the beam combiner, a composite input beam of a multiplicity of non-mutually coherent, spatially concentrated laser pulses and the directing including receiving, at a beam distributor, the composite input beam of the multiplicity of non-mutually coherent, spatially concentrated laser pulses and directing, using the beam distributor, a multiplicity of composite output beams of a plurality of the non-mutually coherent, spatially concentrated laser pulses to a corresponding plurality of spatially distinct locations corresponding to the second multiplicity of regions.

Preferably, the optical inspection method also includes operating at least one of the first multiplicity of cameras in a strobed mode governed by the timing of arrival of a corresponding at least one of the composite output beams at at least one of the spatially distinct locations. Additionally, the operating is at least partly governed by the at least one illumination manager.

There is yet further provided in accordance with still another preferred embodiment of the present invention an optical inspection method including imaging, using a first multiplicity of cameras, a second multiplicity of regions on an object, combining, using at least one illumination manager, illumination from a third multiplicity of illumination sources and separately directing, using the at least one illumination manager, the illumination from the third multiplicity of illumination sources to the second multiplicity of regions, the combining including receiving, at a beam combiner, the illumination from the third multiplicity of illumination sources and providing, using the beam combiner, a composite input beam of a multiplicity of non-mutually coherent, spatially concentrated laser pulses and the separately directing including receiving, at a moving minor, the composite input beam of the multiplicity of non-mutually coherent, spatially concentrated laser pulses and directing, using the moving mirror, a multiplicity of composite output beams of a plurality of the non-mutually coherent, spatially concentrated laser pulses to a corresponding plurality of spatially distinct locations corresponding to the second multiplicity of regions.

In accordance with a preferred embodiment of the present invention the optical inspection method also includes operating at least one of the first multiplicity of cameras in a strobed mode governed by the timing of arrival of a corresponding at least one of the composite output beams at at least one of the spatially distinct locations. Additionally, the operating is at least partly governed by the at least one illumination manager.

BRIEF DESCRIPTION OF THE DRAWINGS

The present invention will be understood and appreciated more fully from the detailed description which follows, taken in conjunction with the drawings in which:

FIGS. 2A, 2B, 2C and 2D are simplified illustrations of four alternative exemplary embodiments of the optical inspection system of FIG. 1.

DETAILED DESCRIPTION OF PREFERRED EMBODIMENTS

Figure 1:
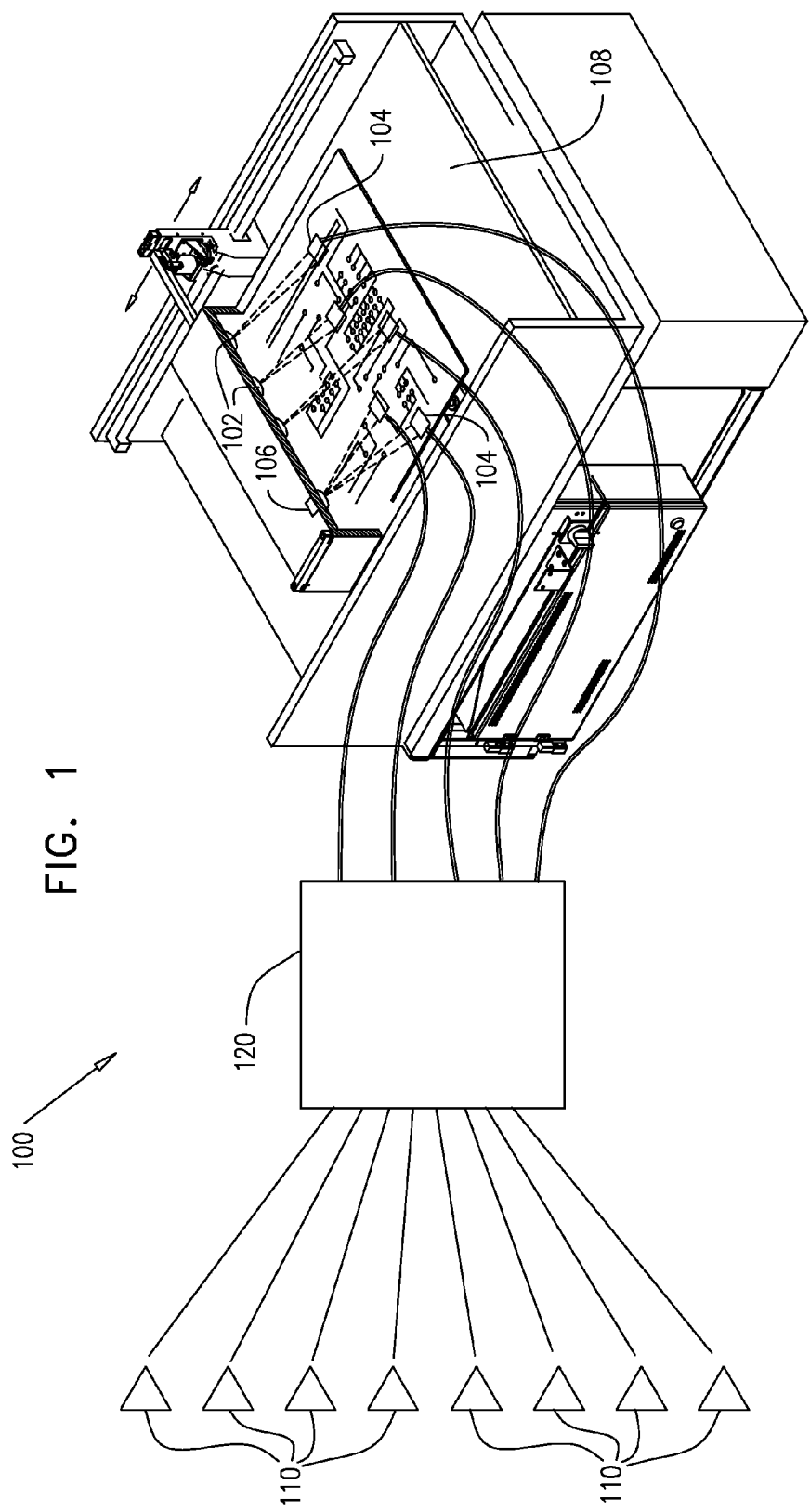
FIG. 1 is a simplified concept level illustration of an optical inspection system constructed and operative in accordance with a preferred embodiment of the invention.

Reference is now made to FIG. 1, which is a simplified concept level illustration of an optical inspection system constructed and operative in accordance with a preferred embodiment of the invention.

As seen in FIG. 1, there is provided an optical inspection system 100 including a first multiplicity of cameras 102, such as CCD or CMOS cameras, operative to image a second multiplicity of regions 104 on an object. Typically, the first multiplicity is equal to the second multiplicity, in that each camera images a corresponding single region, however, it is possible for a single camera to image multiple regions, each at a different time. In the latter case, each camera 102 may be mechanically mounted on a selectable directional positioner 106, such as a pivotable mount. As a further alternative the object being imaged can be mounted on a movable support 108.

In accordance with a preferred embodiment of the present invention there are provided a third multiplicity of illumination sources 110, such as diode lasers, laser chips and vertical cavity lasers. Preferably, the illumination sources 110 are each pulsed coherent light sources having a high level of brightness. The pulsing of all of the illumination sources is coordinated and synchronized in time. The outputs of the third multiplicity of illumination sources 110 are preferably supplied to at least one illumination manager 120, operative to combine illumination from the third multiplicity of illumination sources 110 and thereafter to separately direct illumination therefrom to the second multiplicity of regions 104.

In accordance with a preferred embodiment of the present invention, the at least one illumination manager 120 includes a beam distributor receiving a composite input beam of a multiplicity of non-mutually coherent, spatially concentrated laser pulses and directing a multiplicity of composite output beams of a plurality of the non-mutually coherent, spatially concentrated laser pulses to a corresponding plurality of spatially distinct locations corresponding to the second multiplicity of regions 104.

In accordance with a preferred embodiment of the present invention at least one of the first multiplicity of cameras 102 operates in a strobed mode, under the control of the at least one illumination manager 120, governed by the timing of arrival of a corresponding one of the multiplicity of composite output beams of the plurality of the non-mutually coherent, spatially concentrated laser pulses at a corresponding one of the plurality of spatially distinct locations corresponding to the second multiplicity of regions 104.

Reference is now made to FIGS. 2A, 2B, 2C and 2D, which are simplified illustrations of four alternative exemplary embodiments of the optical inspection system of FIG. 1.

Figure 2A:
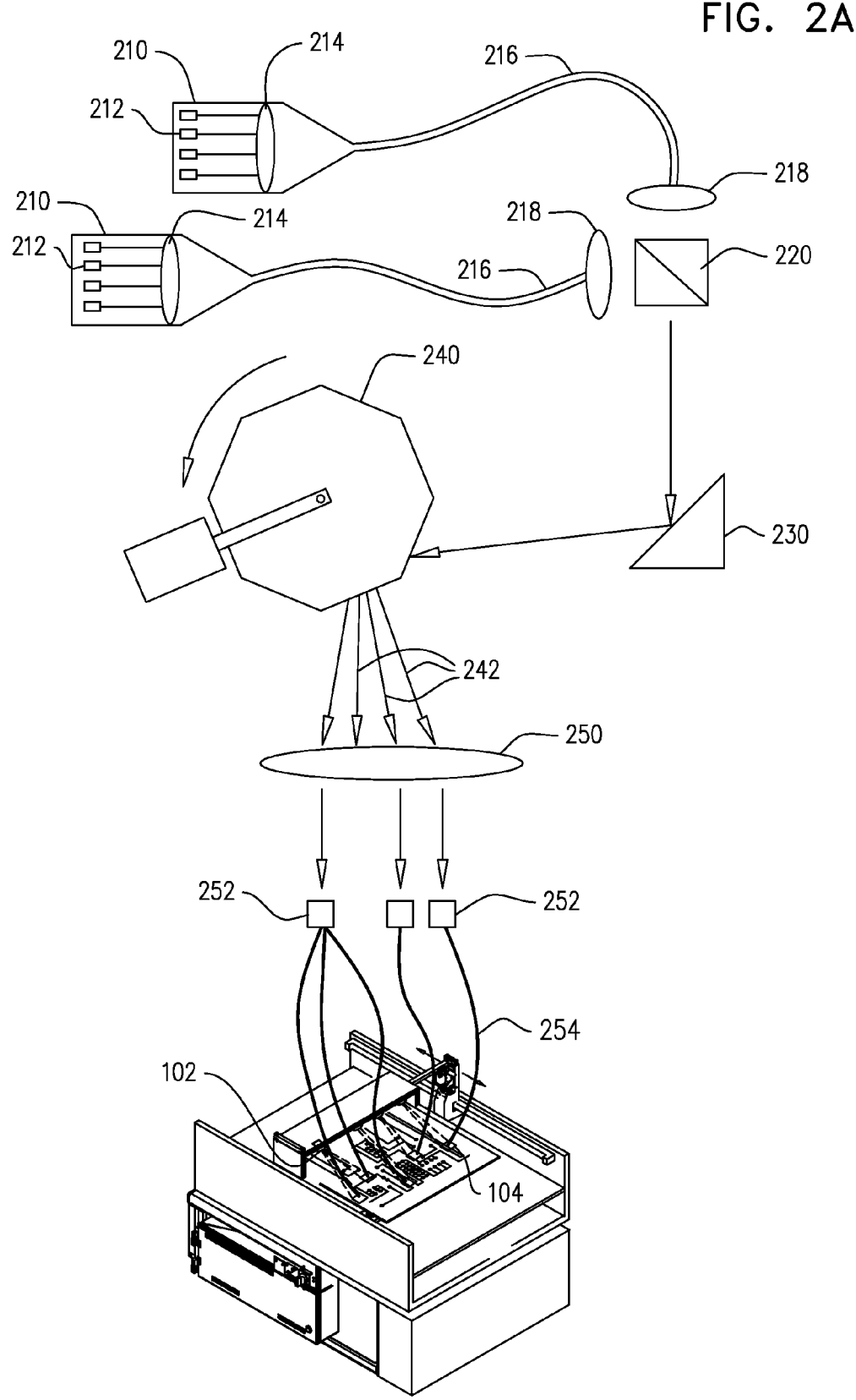

Turning to FIG. 2A, it is seen that there a provided a pair of illumination modules 210. Each illumination module 210 preferably comprises a matrix of pulsed diode lasers 212, typically 90 in number, arranged such that their mutually synchronized output beam pulses are directed through a condensing lens 214, a fiber optic bundle or liquid core fiber 216 and a collimating lens 218. The combined outputs of collimating lenses 218 of each illumination module 210 are pulsed in a mutually synchronized manner and are combined in a polarizing beam combiner 220. The output of the polarizing beam combiner 220 is a synchronized pulsed combined beam formed of typically 180 individual laser beams but having a reduced amount of speckle as compared with the speckle of a single one of the individual laser beams.

The pulsed output of the polarizing beam combiner 220 is directed via a folding mirror 230 to a rotating polygon minor 240, which provides a plurality of mutually angularly spaced pulsed output beams 242, which are directed through a collimating lens 250 to a plurality of power splitting fiber bundles 252, such as a M4G3-1000S-SD fiber optic light guide, commercially available from Schott Moritex Corp., Elmsford, N.Y., USA. Each of the power splitting fiber bundles 252 is split into a plurality of sub-bundles 254, each of which sub-bundles is directed to a given one of the second multiplicity of regions 104, which is viewed by cameras 102.

Figure 2B:
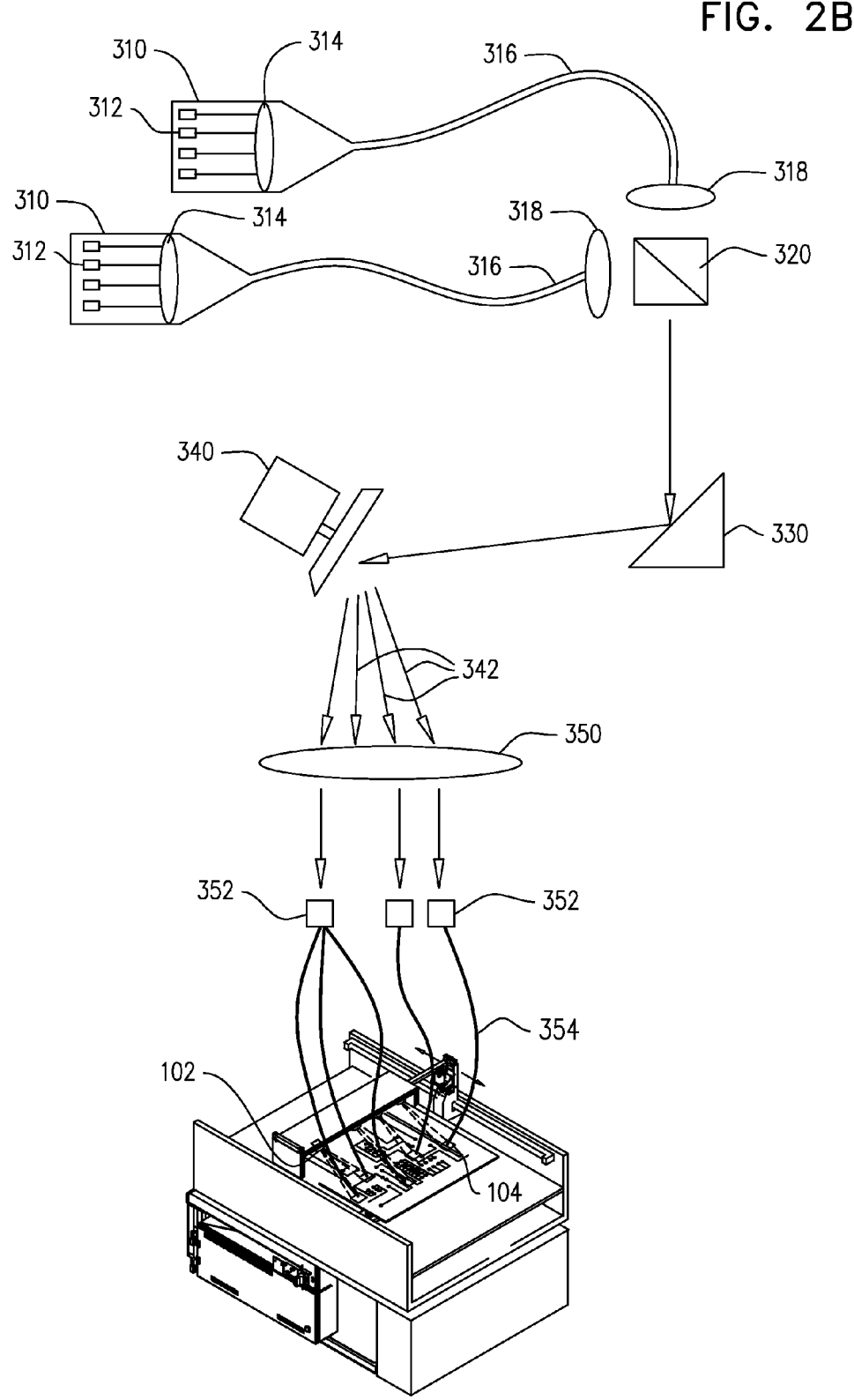

Turning to FIG. 2B, it is seen that there a provided a pair of illumination modules 310. Each illumination module 310 preferably comprises a matrix of pulsed diode lasers 312, typically 90 in number, arranged such that their mutually synchronized output beam pulses are directed through a condensing lens 314, a fiber optic bundle or liquid core fiber 316 and a collimating lens 318. The combined outputs of collimating lenses 318 of each illumination module 310 are pulsed in a mutually synchronized manner and are combined in a polarizing beam combiner 320. The output of the polarizing beam combiner 320 is a synchronized pulsed combined beam formed of typically 180 individual laser beams but having a reduced amount of speckle as compared with the speckle of a single one of the individual laser beams.

The pulsed output of the polarizing beam combiner 320 is directed via a folding mirror 330 to a fast steering minor 340, such as that described in U.S. Pat. No. 7,598,688, which provides a plurality of mutually angularly spaced pulsed output beams 342, which are directed through a collimating lens 350 to a plurality of power splitting fiber bundles 352, such as a M4G3-1000S-SD fiber optic light guide, commercially available from Schott Moritex Corp., Elmsford, N.Y., USA. Each of the power splitting fiber bundles 352 is split into a plurality of sub-bundles 354, each of which sub-bundles is directed to a given one of the second multiplicity of regions 104, which is viewed by cameras 102.

Figure 2C:
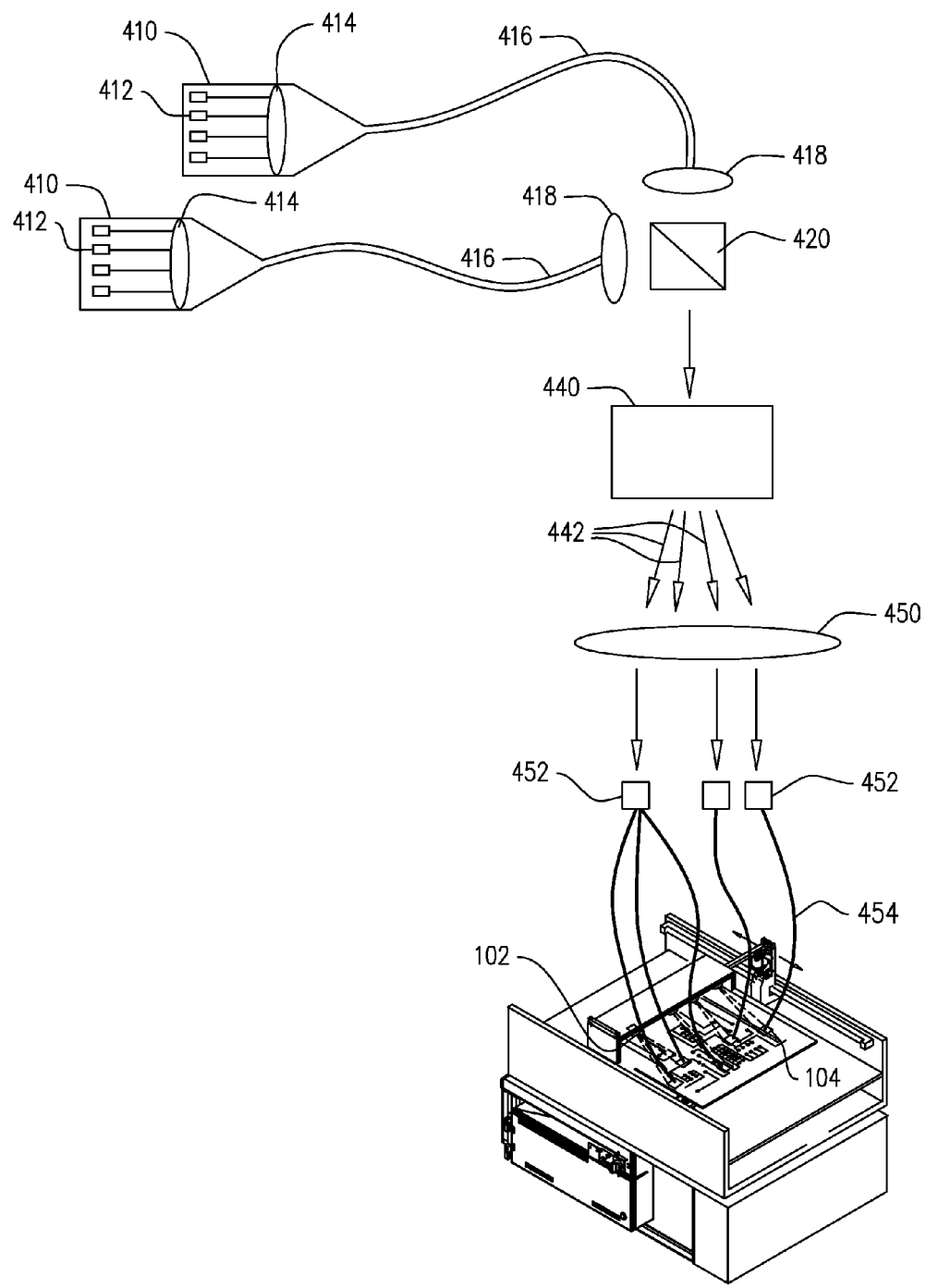

Turning to FIG. 2C, it is seen that there a provided a pair of illumination modules 410. Each illumination module 410 preferably comprises a matrix of pulsed diode lasers 412, typically 90 in number, arranged such that their mutually synchronized output beam pulses are directed through a condensing lens 414, a fiber optic bundle or liquid core fiber 416 and a collimating lens 418. The combined outputs of collimating lenses 418 of each illumination module 410 are pulsed in a mutually synchronized manner and are combined in a polarizing beam combiner 420. The output of the polarizing beam combiner 420 is a synchronized pulsed combined beam formed of typically 180 individual laser beams but having a reduced amount of speckle as compared with the speckle of a single of the individual laser beams.

The pulsed output of the polarizing beam combiner 420 is directed to an acousto-optic modulator 440, which provides a plurality of mutually angularly spaced pulsed output beams 442, which are directed through a collimating lens 450 to a plurality of power splitting fiber bundles 452, such as a M4G3-1000S-SD fiber optic light guide, commercially available from Schott Moritex Corp., Elmsford, N.Y., USA. Each of the power splitting fiber bundles 452 is split into a plurality of sub-bundles 454, each of which sub-bundles is directed to a given one of the second multiplicity of regions 104, which is viewed by cameras 102.

Turning to FIG. 2D, it is seen that there a provided a pair of illumination modules 510. Each illumination module 510 preferably comprises a matrix of pulsed diode lasers 512, typically 90 in number, arranged such that their mutually synchronized output beam pulses are directed through a condensing lens 514, a fiber optic bundle or liquid core fiber 516 and a collimating lens 518. The combined outputs of collimating lenses 518 of each illumination module 510 are pulsed in a mutually synchronized manner and are combined in a polarizing beam combiner 520. The output of the polarizing beam combiner 520 is a synchronized pulsed combined beam formed of typically 180 individual laser beams but having a reduced amount of speckle as compared with the speckle of a single of the individual laser beams.

The pulsed output of the polarizing beam combiner 520 is directed via a folding mirror 530 to a monogon mirror 532, such as an SMP3010 fast minor positioner/scanner, commercially available from SignalTronix, Carlsbad, Calif., USA, which is rotated about an axis 534 and provides a plurality of mutually angularly spaced pulsed output beams 542, which are directed through a collimating lens 550 to a plurality of power splitting fiber bundles 552, such as a M4G3-1000S-SD fiber optic light guide, commercially available from Schott Moritex Corp., Elmsford, N.Y., USA. Each of the power splitting fiber bundles 552 is split into a plurality of sub-bundles 554, each of which sub-bundles is directed to a given one of the second multiplicity of regions 104, which is viewed by cameras 102.

Figure 3:
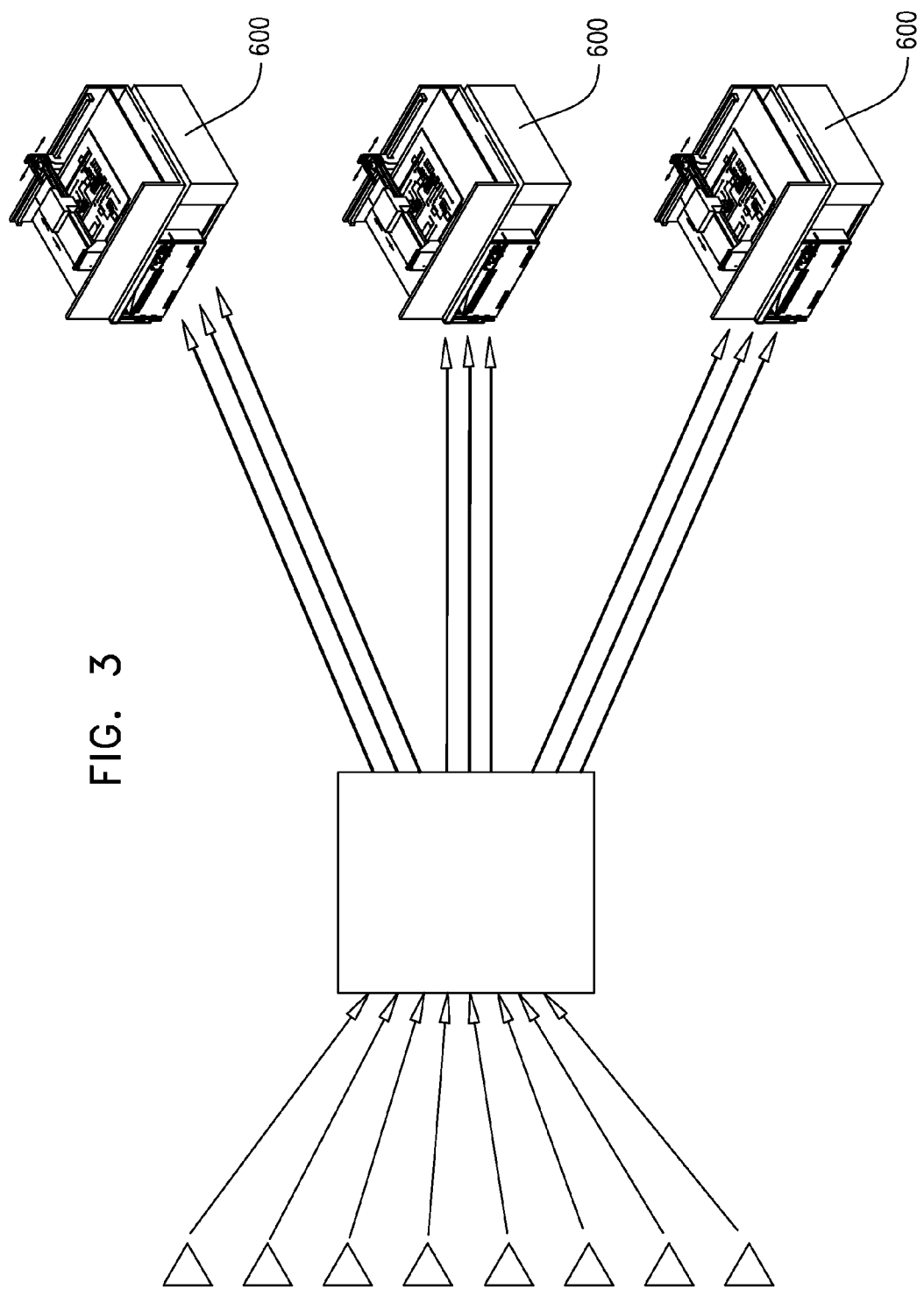
FIG. 3 is a simplified illustration of a centralized illumination system serving multiple optical inspection machines.

Reference is now made to FIG. 3, which is a simplified illustration of a centralized illumination system serving multiple optical inspection machines. As seen in FIG. 3, the system of FIG. 1 generally and more specifically of any of FIGS. 2A-2D may be used to supply high brightness, low speckle illumination to a multiplicity of regions which, may, as shown, be located on multiple disparate inspection machines. For example, in the embodiment in FIG. 2A, power splitting fiber bundles 252 may each be directed to inspection locations on a different inspection machine 600. In such a case, each of power splitting fiber bundles 252 may be split into a plurality of sub-bundles 254 at each machine 600, each of which sub-bundles 254 being directed to a given one of the second multiplicity of regions 104 at that machine 600, which is viewed by a camera 102.

It will be appreciated by persons skilled in the art that the present invention is not limited to what has been particularly shown and described hereinabove. Rather the scope of the invention includes both combinations and subcombinations of the various features described hereinabove as well as modifications and variations thereof which would occur to persons skilled in the art upon reading the foregoing description and which are not in the prior art.

The invention claimed is:

1. An optical inspection system comprising:
   a plurality of cameras operative to image a plurality of spatially distinct regions on an object;
   a plurality of illumination sources which output a plurality of laser pulses; and
   at least one illumination manager operative to combine illumination from said plurality of illumination sources into a single composite input beam and thereafter to direct the illumination from said plurality of illumination sources to said plurality of spatially distinct regions,
   said at least one illumination manager comprising:
      a beam distributor configured to receive the composite input beam, to separate the composite input beam into a plurality of composite output beams, the plurality of composite output beams all being substantially identical, and to direct the plurality of composite output beams to the plurality of spatially distinct regions, respectively.

2. An optical inspection system according to claim 1 and wherein said beam distributor is a time and space beam distributor.

3. An optical inspection system according to claim 1 and wherein said beam distributor is a time beam distributor.

4. An optical inspection system according to claim 1 and wherein said beam distributor is a space beam distributor.

5. An optical inspection system according to claim 1 and wherein said beam distributor comprises a polygon mirror.

6. An optical inspection system according to claim 1 and wherein said beam distributor comprises a monogon mirror.

7. An optical inspection system according to claim 1 and wherein at least one of said plurality of cameras operates in a strobed mode governed by a timing of arrival of a corresponding at least one of said composite output beams at at least one of said spatially distinct regions.

8. An optical inspection system according to claim 7 and wherein operation of said at least one of said plurality of cameras in said strobed mode is controlled by said at least one illumination manager.

9. An optical inspection system comprising:
   a plurality of cameras operative to image a plurality of spatially distinct regions on an object;
   a plurality of illumination sources which output a plurality of laser pulses; and
   at least one illumination manager operative to combine illumination from said plurality of illumination sources into a single composite illumination beam and thereafter to separately direct the illumination from said plurality of illumination sources to said plurality of spatially distinct regions,
   said at least one illumination manager comprising:
      a moveable mirror configured to receive the composite input beam, to direct a plurality of composite output beams to the plurality of spatially distinct regions.

10. An optical inspection system according to claim 9 and wherein said at least one illumination manager comprises a polygon mirror.

11. An optical inspection system according to claim 9 and wherein said at least one illumination manager comprises a monogon mirror.

12. An optical inspection system according to claim 9 and wherein at least one of said plurality of cameras operates in a strobed mode governed by a timing of arrival of a corresponding at least one of said composite output beams at at least one of said spatially distinct regions.

13. An optical inspection system according to claim 12 and wherein operation of said at least one of said plurality of cameras in said strobed mode is controlled by said at least one illumination manager.

14. An optical inspection method comprising:
imaging, using a plurality of cameras, a plurality of spatially distinct regions on an object;
combining, using at least one illumination manager, a plurality of laser pulses from a plurality of illumination sources into a single composite input beam; and
directing, using said at least one illumination manager, illumination from said plurality of illumination sources onto said plurality of spatially distinct regions,
said combining comprising:
receiving, at a beam combiner, said a plurality of non-mutually coherent, spatially concentrated laser pulses from said plurality of illumination sources; and
providing, using said beam combiner, the composite input beam; and
wherein said directing the illumination from said plurality of illumination sources onto said plurality of spatially distinct regions comprises:
receiving, at a beam distributor, said composite input beam;
separating the composite input beam into a plurality of composite output beams, the plurality of composite output beams all being substantially identical, and
directing, using said beam distributor, the plurality of composite output beams to said plurality of spatially distinct regions, respectively.

15. An optical inspection method according to claim 14 and also comprising:
operating at least one of said plurality of cameras in a strobed mode governed by a timing of arrival of a corresponding at least one of said composite output beams at at least one of said spatially distinct regions.

16. An optical inspection method according to claim 15 further comprising controlling said operating using said at least one illumination manager.

17. An optical inspection method comprising:
imaging, using a plurality of cameras, a plurality of spatially distinct regions on an object;
combining, using at least one illumination manager, a plurality of laser pulses from a plurality of illumination sources into a single composite input beam; and
separately directing, using said at least one illumination manager, illumination from said third multiplicity of illumination sources to said second multiplicity of regions,
said combining comprising:
receiving, at a beam combiner, said illumination from said third multiplicity of illumination sources; and
providing, using said beam combiner, a single composite input beam of a multiplicity of non-mutually coherent, spatially concentrated laser pulses; and
said separately directing comprising:
receiving, at a moving mirror, said single composite input beam of said multiplicity of non-mutually coherent, spatially concentrated laser pulses; and
directing, using said moving mirror, a multiplicity of composite output beams of a plurality of said non-mutually coherent, spatially concentrated laser pulses to a corresponding plurality of spatially distinct locations corresponding to said second multiplicity of regions.

18. An optical inspection method according to claim 17 and also comprising:
operating at least one of said first multiplicity of cameras in a strobed mode governed by the timing of arrival of a corresponding at least one of said composite output beams at at least one of said spatially distinct locations.

19. An optical inspection method according to claim 18 and wherein said operating is at least partly governed by said at least one illumination manager.

\* \* \* \* \*